(12) United States Patent
Yu et al.

(10) Patent No.: US 8,812,240 B2
(45) Date of Patent: Aug. 19, 2014

(54) DOSE DISTRIBUTION MODELING BY REGION FROM FUNCTIONAL IMAGING

(75) Inventors: Shipeng Yu, Exton, PA (US); Glenn Fung, Madison, WI (US); Steven Florian Petit, Maastricht (NL); Hugo J. W. L. Aerts, Maastricht (NL); Claudia Offermann, Kerkrade (NL); Michel Oellers, Sint Joost (NL); Philippe Lambin, Genappe-Bousval (BE); Dirk de Ruysscher, Tervuren (BE); Andreas Lubbertus Aloysius Johannes Dekker, Maastricht (NL); Sriram Krishnan, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1027 days.

(21) Appl. No.: 12/398,487

(22) Filed: Mar. 5, 2009

(65) Prior Publication Data

US 2009/0234626 A1    Sep. 17, 2009

Related U.S. Application Data

(60) Provisional application No. 61/036,266, filed on Mar. 13, 2008.

(51) Int. Cl.
| | |
|---|---|
| *G01N 33/48* | (2006.01) |
| *G01N 31/00* | (2006.01) |
| *G06G 7/48* | (2006.01) |
| *G06G 7/58* | (2006.01) |
| *A61N 5/10* | (2006.01) |
| *G06F 19/00* | (2011.01) |
| *G06N 99/00* | (2010.01) |
| *G06T 11/00* | (2006.01) |

(52) U.S. Cl.
CPC .......... *A61N 5/1031* (2013.01); *G06F 19/3437* (2013.01); *G06N 99/005* (2013.01); *G06T 11/00* (2013.01)
USPC ..................... 702/19; 702/22; 703/11; 703/12

(58) Field of Classification Search
CPC .. G06F 19/3437; G06N 99/005; G06T 11/00; A61B 5/0075; A61B 5/055; A61B 2019/5236
See application file for complete search history.

(56) References Cited

U.S. PATENT DOCUMENTS 7,461,048 B2 * 12/2008 Teverovskiy et al. ........... 706/62
7,636,420 B2 * 12/2009 Spies et al. ...................... 378/65

(Continued)

OTHER PUBLICATIONS

Strauss et al. (Eur. J. Nucl. Med. Mol. Imaging, 2007, 34, 868-877).*

(Continued)

*Primary Examiner* — Larry D Riggs, II
(74) *Attorney, Agent, or Firm* — Joshua B Ryan

(57) ABSTRACT

Functional imaging information is used to determine a probability of residual disease given a treatment. The functional imaging information shows different characteristic levels for different regions of the tumor. The probability is output for planning use and/or used to automatically determine dose by region. Using the probability, the dose may be distributed by region so that some regions receive a greater dose than other regions. This distribution by region of dose more likely treats the tumor with a same dose, allows a lesser dose to sufficient treat the tumor, and/or allows a greater dose with a lesser or no increase in risk to normal tissue. The dose plan may account for personalized tumors as each patient may have distinct tumors. Probability of dose application accuracy may also be used, so that a combined treatment probability allows efficient dose planning.

23 Claims, 6 Drawing Sheets

(56) References Cited

U.S. PATENT DOCUMENTS

| | | | |
|---|---|---|---|
| 7,639,854 B2* | 12/2009 | Schnarr et al. | 382/128 |
| 2003/0120458 A1 | 6/2003 | Rao et al. | |
| 2008/0214933 A1* | 9/2008 | Von Busch et al. | 600/431 |

OTHER PUBLICATIONS

Chelikani et al., (Int. J. Radiation Oncology Biol. Phys., 2006, 65, 2, 535-547).*

Alber et al. (Physics in Medicine and Biology, 2003, 48, N31-N35).*

Morris et al. (Journal of Computers, 2006, 1(7), 21-31).*

Bentzen, "Theragnostic imaging for radiation oncology: dose-painting by numbers", Lancet Oncol 6 (2005) 112-117.

Ling et al., "Towards multidimensonal radiotherapy (MD-CRT): biological imaging and biolgical conformality", Int J Radiat Oncol Biol Phys 47 (2000) 551-560.

Vaupel et al., "Blood flow, oxygen and nutrient supply, and metabolic microenvironment of human tumors: a review", Cancer Res 49 (1989) 6449-6465.

Brizel et al., "Tumor hypoxia adversely affects the prognosis of carcinoma of the head and neck", Int J Radiat Oncol Biol Phys 38 (1997) 285-289.

Magagnin et al., "Patterns of tumor oxygenation and their influence on the cellular hypoxic response and hypoxia-directed therapies", Drug Resist Updat 9 (2006) 185-197.

Rasey et al, "Characterization of radiolabeled fluoromisonidazole as a probe for hypoxic cells", Radiat Res 111 (1987) 292-304.

Bentzen et al., "Assessment of hypoxia in experimental mice tumours by [18F]fluoromisonidazole PET and pO2 electrode measurements, Influence of tumour volume and carbogen breathing", Acta Oncol 41 (2002) 304-312.

Rajendran et al., "Tumor hypoxia imaging with [F-18] fluoromisonidazole positron emission tomography in head and neck cancer", Clin Cancer Res 12 (2006) 5435-5441.

Dubois et al., "Evaluation of hypoxia in an experimental rat tumour model by [(18)F]fluoromisonidazole PET and immunohistochemistry", Br J Cancer 91 (2004) 1947-1954.

Zimmy et al., "FDG—a marker of tumour hypoxia? A comparison with [(18)F]fluoromisonidazole and pO (2)-polarography in metastatic head and neck cancer", Eur J Nucl Med Mol Imaging 33 (2006) 1426-1431.

Eschmann et al., "Prognostic impact of hypoxia imaging with 18F-misonidazole PET in non-small cell lung cancer and head and neck cancer before radiotherapy", J Nucl Med 46 (2005) 253-260.

Webb et al., "A model for calculating tumour control probability in radiotherapy including the effects of inhomogeneous distributions of dose and clonogenic cell density", Phys Med Biol 38 (1993) 653-666.

Wouters et al., "Cells at intermediate oxygen levels can be more important than the "hypoxic fraction" in determining tumor response to fractionated radiotherapy", Radiat Res 147 (1997) 541-550.

Alber et al., "On biologically conformal boost dose optimization", Phys Med Biol 48 (2003) N31-35.

Rodrigues et al., "Prediction of radiation pneumonitis by dose—Volume histogram parameters in lung cancer—a systematic review", Radiother Oncol 71 (2004) 127-138.

Thorwarth et al., "Hypoxia dose painting by numbers: a planning study", Int J Radiat Oncol Biol Phys. May 1, 2007;68(1): 291-300.

PET-CT—Positron emission tomography—computed tomography; Wikipedia http://en.wikipedia.org/wiki/Positron_emission_tomography_-_computed_tomography; Feb. 4, 2009.

Kutcher et al., "Calculation of Complication Probability Factors for Non-Uniform Normal Tissue Irradiation: The Effective Volume Method", Int. J. Radiation Oncology Biol. Phys., vol. 16, (1989) pp. 1623-1630.

Goitein et al., "Strategies for Treating Possible Tumor Extension: Some Theoretical Considerations", Int. J. Radiation Oncology Biol. Phys., vol. 11 (1985) pp. 1519-1528.

* cited by examiner

DOSE DISTRIBUTION MODELING BY REGION FROM FUNCTIONAL IMAGING

RELATED APPLICATIONS

The present patent document claims the benefit of the filing date under 35 U.S.C. §119(e) of Provisional U.S. Patent Application Ser. No. 61/036,266, filed Mar. 13, 2008, which is hereby incorporated by reference.

BACKGROUND

The present embodiments relate to dose modeling. Dose levels are used for different types of therapy to treat cancer or other tumors. For example, radiation, laser, chemotherapy, or other therapies use different dose levels to treat (destroy or reduce) a tumor while minimizing the effects on healthy tissue.

The delivery of radiotherapy evolved from therapy designed based primarily on two dimensional x-ray images. Increasingly complex computer algorithms determine dose using three-dimensional x-ray based images. Advances in imaging technologies and the introduction of intensity modulated radiation therapy (IMRT) enable therapy planning with large amounts of data. In addition, greater awareness of the challenges to the accuracy of the treatment planning process, such as problems with set-error and organ movement, have begun to be systematically addressed. Four-Dimensional Radiotherapy or Image guided radiotherapy (IGRT) account for the tumor size and shape in therapy planning.

Image-guided radiation therapy is dependent on serial image datasets acquired using any of a variety of medical imaging platforms. Magnetic resonance imaging (MRI), computed tomography (CT), or ultrasound may be used. Other medical imaging includes functional imaging, such as positron emission tomography (PET). With PET, functional information can be correlated with anatomic localization from another modality, such as CT. As imaging datasets become more sophisticated, the therapy plan may account for the size and 3D and 4D positions of the target and normal structures. Real- or near-real-time positional re-planning of the radiation treatment localization coordinates may be provided. However, even with better position information, patients may still suffer normal tissue damage due to the therapy.

A malignant tumor is not a homogeneous mass, but is composed of regions that differ in tumor cell density, normal tissue involvement, vasculature, hypoxia, and gene expression. This biological heterogeneity results in large differences in the sensitivity of regions within the tumor to treatment with radiotherapy, chemotherapy, or new targeted agents. With non-invasive imaging and profiling, this intra-tumor heterogeneity may be identified. This has lead to the concept of "Biological Target Volume." However assessing a link between images and the radio-sensitivity of different tissue regions (or voxels) is not straightforward. Because of the limited spatial resolution of imaging techniques (e.g., typically >1 $mm^3$), it is uncertain whether the voxels around the tumor contain clonogenic cells. Moreover, the knowledge about how the different biological parameters influence radio-sensitivity on a voxel level is limited.

SUMMARY

In various embodiments, systems, methods, instructions, and computer readable media are provided for modeling dose distribution and/or distributing dose for tumor treatment. Functional imaging information shows different characteristic levels for different regions of the tumor. The functional imaging information is used to determine a probability of residual disease given a treatment. The probability is output for planning use and/or used to determine, automatically, dose by region. Using the probability, the dose may be distributed by region so that some regions receive a greater dose than other regions. This distribution by region of dose more likely treats the tumor with a same dose, allows a lesser dose to sufficiently treat the tumor, and/or allows a greater dose with a lesser or no increase in risk to normal tissue. The dose plan may account for the distinct tumor of a given patient. Probability of dose application accuracy may also be used, so that a combined treatment probability allows efficient dose planning.

In a first aspect, a system for modeling dose distribution is provided. An input is operable to receive functional imaging information representing metabolic or biochemical activity of a tumor. A processor is operable to apply a model of tumor response to a dose of radiation. The tumor response is different for different regions of the tumor as a function of the functional imaging information. A display is operable to output an image as a function of the tumor response.

In a second aspect, a computer readable storage medium has stored therein data representing instructions executable by a programmed processor for distributing dose for tumor treatment. The instructions include receiving positron emission information showing variance of standardized uptake of different locations in a cancer region. Therapy responses of the cancer region at the different locations are predicted as a function of the standardized uptake for the respective different locations. An increase or decrease in a location specific radiation dose is determined as a function of the predicted therapy response. The location specific radiation dose is output for each of the different locations of the cancer region.

In a third aspect, a method is provided for modeling dose distribution. Uptake of an agent at different portions of a tumor in a patient is determined from emission tomography information. Radiation response of the different portions of the tumor is classified as a function of the uptake for the different portions and control probabilities of residual disease given a dose. The control probabilities are machine-learned from a dataset for other patients having uptake information before and after treatment by radiation. Dose information is determined as a function of the radiation response. The dose information varies between the different portions of the tumor. The dose information is output for use with a linear accelerator to treat the patient.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Figure 1:
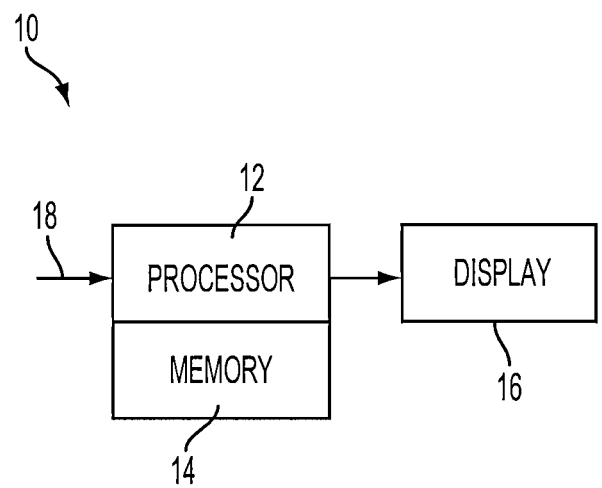
FIG. 1 is a block diagram of one embodiment of a system for modeling dose distribution.

Intra-tumor heterogeneity allows therapeutic possibilities for individualized patient treatment. Today, radiation is given to the tumor at a more or less homogeneous dose (e.g., the tumor receives from 95%-107% of the prescribed dose at the isocenter of the beam). Cells that are resistant receive the same dose as the more sensitive cells, resulting in unneeded dose to the sensitive areas and to a non-effective dose to the resistant parts of a tumor. As the total radiation dose is restricted by virtue of the normal tissue constraints, dose redistribution (higher dose to resistant and lower dose to sensitive areas) within the tumor may provide better treatment. Assessing heterogeneity with 3D or 4D imaging methods, therapy is designed to target the most resistant regions of the tumor, for example by redistributing or boosting the radiation dose to more resistant areas. Instead of a "binary" approach (i.e., parts of the tumor are considered to be resistant or not), the gradients of resistance throughout the tumor are used. The dose is redistributed to the tumor to match the differences in radio-sensitivity. The spatial distribution or dose painting is performed using probability.

A voxel control probability is determined, showing the probability for treatment/disease residual by location. The response of a voxel (i.e., three-dimensional region of the tumor established by imaging settings) to radiation depends on the contents of the voxel and the radiation dose. The radio-sensitivity of a voxel may be uncertain, so is described in a probabilistic manner. Voxel control/complication probability (VCP) analogue to tumor control/complication probability is used. The VCP describes the probability of voxel control/complication as function of the delivered dose to the voxel.

For example, a quantitative relation between fluoro-18 deoxyglucose (FDG) uptake in the tumor, dose, and a tumor control probability may guide tumor dose redistribution in non-small cell lung cancer (NSCLC). Local tumor failure may occur in the majority of locally advanced NSCLC patients treated with chemo or radiation therapy. Treatment efficacy may be improved by redistributing dose from radiosensitive tumor regions to radio-resistant tumor regions without increasing the dose to normal tissue. The likelihood of residual disease three months after therapy is largest in the regions that correspond to high (FDG) uptake zones in the primary tumor before the start of therapy. FDG uptake indicates regions for increasing and decreasing the dose. The voxel control probability (e.g., a quantitative relation between FDG uptake in a voxel and successful treatment) before the start of radiotherapy, delivered dose to the voxel, and the probability of residual disease in that voxel three months or other time after therapy guide tumor dose redistribution.

In addition to heterogeneity of the tumor, the uncertainties in application of the dose to the tumor may be dealt with probabilistically. Integrating dose uncertainties and tumor heterogeneity in Voxel control/complication probability guided radiotherapy (VCP-GRT) may provide for better dose planning. Margins are provided in radiotherapy to account for the uncertainties in tumor delineation, position, and shape as well as uncertainties in the delivery and planning phase of radiotherapy. These uncertainties of radiotherapy planning and delivery may be included in a probabilistic manner. VCP-GRT, which is based on a double probabilistic approach, may integrate clinical and biological data as well as systemic treatment. This approach is "data-based" and may be independent of any a priori hypothesis.

Radiation Oncology may be based on at least three "probability maps." One map is derived from fused images before and during treatment. The fused information provides a probability of relapse per voxel. This is an "imaging based VCP." Another map is of dose probability on the tumor and the normal tissues. The dose probability provides a "dose distribution based VCP" or "uncertainty based planning." Another map is an "imaging-dose based VCP" integrating both probabilities. Further refinements account for the effect of systemic treatments, and/or other biological and genetic factors.

Probability may include an actual probability, such as a value from 0 to 1, but may alternatively include a score or other value related, at least in part, to the likelihood or chance. Displays, outputs, images or values of probability may be normalized and/or represent the likelihood with or without consideration for other factors. For example, a score based on other factors and a probability may be an indication of probability.

The embodiments described herein may use just the probability information associated with heterogeneity of the tumor. In other embodiments, both voxel control and dose uncertainty probabilities are used. The embodiments model dose distribution by creating a model to provide the probabilities, by applying the model to indicate probable treatment success, and/or by applying the model to recommend dose distribution.

FIG. 1 shows is a block diagram of an example system 10 for modeling dose distribution. The system 10 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated workflows are provided to assist a user in generating a predication of treatment outcome and/or recommending dose. Data representing a patient is transformed into an image or data indicating effectiveness of treatment.

The system 10 is a computer, personal computer, server, PACs workstation, imaging system, medical system, network processor, network, or other now know or later developed processing system. The system 10 includes at least one processor (hereinafter processor) 12, at least one memory (hereinafter memory) 14, a display 16, and at least one input (hereinafter input) 18. Additional, different, or fewer components may be provided.

The processor 12 is implemented on a computer platform having hardware components. The computer platform also includes an operating system and microinstruction code. The various processes, methods, acts, and functions described herein may be either part of the microinstruction code or part of a program (or combination thereof) which is executed via the operating system.

The input 18 is a user input, network interface, external storage, or other input device for providing data to the system 10. For example, the input 18 is a mouse, keyboard, track ball, touch screen, joystick, touch pad, buttons, knobs, sliders, combinations thereof, or other now known or later developed user input device. The user input operates as part of a user interface. For example, one or more buttons are displayed on the display 16. The user input is used to control a pointer for selection and activation of the functions associated with the buttons. Alternatively, hard coded or fixed buttons may be used. As another example, the input 18 is a hard-wired or wireless network interface. A universal asynchronous receiver/transmitter (UART), a parallel digital interface, a software interface, Ethernet, or any combination of known or later developed software and hardware interfaces may be used. The network interface may be linked to various types of networks, including a local area network (LAN), a wide area network (WAN), an intranet, a virtual private network (VPN), and the Internet.

The input 18 is an interface to receive data. The data may include clinical information, such as the age, gender, family history, test results, tumor volume, or other information determined to be relevant to the treatment of a tumor. The data may include functional imaging information. Functional imaging information includes an image, data to generate an image, quantities derived from a functional scan, or other data that is a function of functional imaging data. Functional imaging data represents metabolic or biochemical activity of a tumor. For example, positron emission tomography is used with fluorodeoxyglucose (FDG) for scanning a non-small cell lung cancer tumor. The FDG highlights, binds to, or is taken up by glucose, showing glucose metabolism in the PET data. "Uptake" is used to reflect binding, absorption, tagging, labeling, connecting, or other reaction of an agent to the tissue. Other now known or later developed functional imaging modes may be used. Other now known or later developed binding or contrast agents to identify function in the scan region may be used. In alternative embodiments, the imaging modality identifies tissue function based on data processing without introduction of a contrast or binding agent. Other types of tumors may be scanned.

In one embodiment, PET-FDG data is acquired with a CT-PET imaging system. The imaging system generates both CT and PET information for at least an overlapping region. Since the scans are performed with a same system and close in time, the relative position of the PET scan to the CT scan is known. The CT scan provides structural information, such as the location of ribs or bones. Correlation processing may alternatively be used to spatially align functional data with structural data. In other embodiments, manual alignment is provided or the functional data is used without alignment with structural data. Other combinations of imaging modes may be used, such as MRI-PET.

Figure 2:
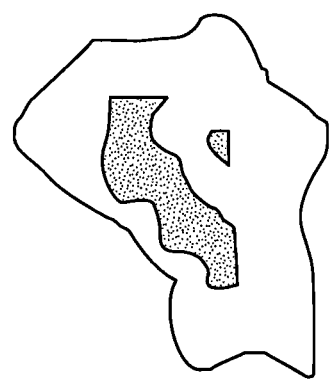
FIG. 2 illustrates an example tumor with a heterogeneous characteristic.
Figure 3:
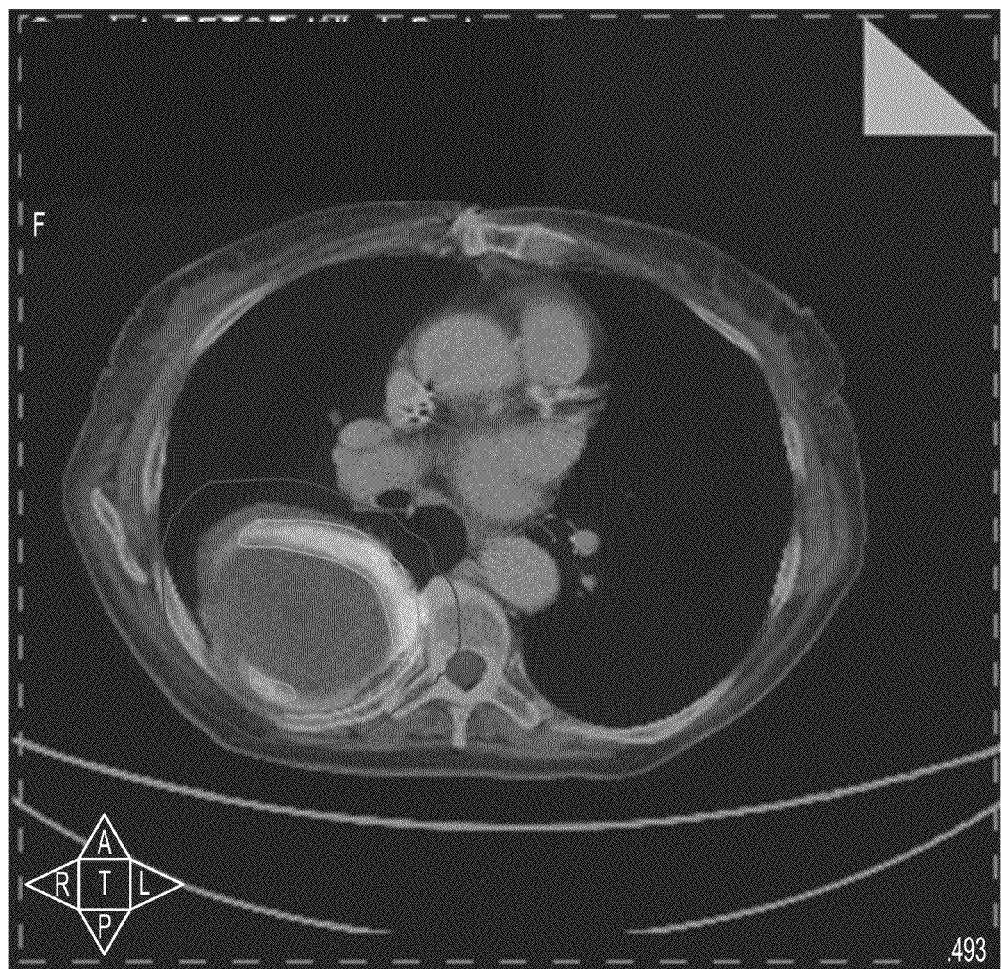
FIG. 3 is an example CT-PET image showing a lung tumor with a heterogeneous characteristic.

FIG. 2 shows an example image from functional data. The darker regions correspond to greater function. For example, the darker regions correspond to greater uptake of FDG. FIG. 3 shows a different tumor in a CT image. A generally oval outer ring surrounds the tumor in the lungs of a patient. The image includes an overlay of functional information. The brighter regions of the tumor are designated by conforming lines. These brighter regions indicate increased function, such as greater uptake of FDG.

The processor 12 has any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 12. The processor 12 implements the program alone or includes multiple processors in a network or system for parallel or sequential processing.

The processor 12 creates a model, applies the model, or both creates and applies the model. The model is of tumor response to a treatment dose. Any type of treatment dose may be modeled, such as radiation, chemotherapy, laser, heat, or other now known or later developed therapies.

The modeled tumor response is different for different regions of the tumor. The functional imaging information is used to create the model, so the model reflects that different portions respond differently to a given dose.

In one embodiment, the model is a machine-learned model, but manually programmed models may be used. Any machine-learning algorithm or approach to classification may be used. For example, a support vector machine, linear regression, boosting network, linear discriminant analysis, relevance vector machine, combinations thereof, or other now known or later developed machine learning is provided. The machine learning provides a matrix or other output. The matrix is derived from analysis of a database of training data with known results, such as a database of data with binary or a larger range of possible labeled outcomes. The machine-learning algorithm determines the relationship of different inputs to the result. The learning may select only a sub-set of input features or may use all available input features. A programmer may influence or control which input features to use. The matrix associates input features with outcomes, providing a model for classifying.

The model represents a probability of residual disease. This probability is of success of the treatment or dose. Other probabilities may be used. Any period may be used for measuring success or reoccurrence, such as 90 days after completion of treatment. Alternatively, the probability is based on measurements during treatment, such a reoccurrence or not after exposure to a partial dose.

Different probabilities may be learned based on the uptake or disease level for the region. For example, probability of reoccurrence given a specific dose is determined for each of four ranges of uptake values. More or fewer levels of increment may be provided. Each probability indicates, based on the initial level of tumor function, the likelihood of residual disease given a dose. Since different regions may have different initial disease function levels, different probabilities are determined.

Residual disease, reoccurrence, or success is measured subjectively, such as by a medical practitioner. Tissue or an image may be examined for any residual disease. Alternatively, the processor 12 determines residual disease. For example, functional imaging information is analyzed to identify an uptake level or function above a threshold amount. The function may be represented by lack of activity, so uptake levels below a threshold amount may indicate no reoccurrence.

The threshold is fixed or predetermined. In other embodiments, the threshold adapts as a function of an input. For example, a corresponding CT image is analyzed to identify spatially aligned functional imaging information from a default or control location, such as the aortic arch in lung imaging. The maximum, minimum, average, mean, median or other uptake value at that region is used to establish the threshold for indication of disease. The threshold for determining the existence of the tumor at a given time is based, at least in part, on the information for that patient at that time. Other regions or threshold determination may be used.

The probability is learned or derived from data for other patients. The database of other patients includes functional imaging data from before therapy and at the desired time after therapy. The dose applied to the tumor and/or regions of the tumor for treatment is also included. Other features may be provided, such as age, gender, WHO performance, lung function (e.g., expiration volume), tumor type, and tumor size. Different feature vectors may be provided for different types of tumors.

In one embodiment, the feature vector for a given region includes the uptake values or other functional imaging information for adjacent regions. For example, a mean, median, variance or other statistical value for a group of locations around a given location is calculated and used as a feature for learning. Any use of neighboring regions may be provided to indicate the likelihood of success of treatment.

In one embodiment, dose boosting based on topography of relapse is used to train the model. For example, metabolically active areas with high Cho/NAA ratio are more likely to correspond to a site of relapse. In lung cancer, the location of metabolically active areas is more likely stable during radiotherapy. Dose may be boosted for these biological target volumes. Boosting tumor areas, which, a priori, have an increased likelihood of failure, may improve treatment outcome. Such a strategy places an important role on biological imaging in order to determine which tumor areas will be more resistant to treatment. The patterns of tumor recurrence within the tumor of many patients with NSCLC or other disease who received chemotherapy followed by radiotherapy or other treatment may be based on repeated FDG-PET-CT scans or other scans.

The tumor may recur in areas that show the most avid FDG uptake before therapy. For example, FIG. 2 represents an FDG image after therapy where the darker regions correspond to disease reoccurrence. Dose boosting may be provided by training the model for probabilities based on a pattern of recurrence post-treatment in treatment position in various pathologies. The model is trained to output a voxel-per-voxel assessment of risk of recurrence.

In one example embodiment of learning a model, data is collected for 95 patients with inoperable NSCLC (stage I-III). These 95 patients were treated with radical radiotherapy alone or with chemo-radiation. In other embodiments, palliative therapy may be used. FDG PET-CT scans are acquired just before the start of radiotherapy (day 0) and three months post-treatment. The total radiation dose may vary between patients, such as being between 54 and 80 Gy. The PET scans of each patient before and after therapy are registered. Any registration may be used, such as minimum sum of absolute differences, cross-correlation, or other measure of alignment. For example, the spatial registration is an automatic rigid registration based on bony landmarks in the proximity of the primary tumor using the CT scans. Non-rigid registration, registration based on speckle or other features, or other registrations may be used. Data for patients where the tumors show large deformations, as determined by observers or an automated measurement, may be excluded from the analysis.

The residual disease of the primary tumor after therapy is defined as the voxels (tumor locations) with a FDG uptake higher than the maximum uptake in the aortic arch or other threshold. The functional imaging information or uptake values may be normalized to the threshold, providing standardized uptake values (SUV). The probability of residual disease in a tumor voxel is determined. The SUV at day 0 ($SUV_0$) for each tumor location is scored by placing values within predefined SUV bandwidths, such as 0-3, 3-7, and greater the 7 indicating three levels of tumor function. The SUV at 90 days after therapy is scored. The probability is determined based on the differences in scores for the various patients. The probability may account for other factors, such as any of the feature vectors used to train the model.

Other approaches may be used for the processor 12 to train the model using probability of residual disease given a dose. In hypothesis-based dose boosting, the probability of the response to radiotherapy of the areas with different biological characteristics, such as hypoxia, EGFR, or stem cell density, is determined. Hypoxia, because of rapid cellular expansion and/or insufficient tumor angiogenesis, may be a biological property in solid tumors. Solid tumors may accelerate malignant progression and metastatic potential of primary carcinomas and lead to increased resistance to cancer therapies. To facilitate treatment guidance in individual patients by a probability-based model, non-invasive functional imaging measures oxygenation levels in solid tumors. One such technique involves PET using radio labeled 2-nitroimidazoles, like [$^{18}$F]Fluoromisonidazole ([$^{18}$F]FMISO). Different tracers (binders or contrast agents) may be used to determine the probabilities from additional functional imaging data and/or feature vectors.

The model may be trained for other probabilities, such as learning a normal tissue complication probability or a probability indicating likelihood of application of dose to the correct location. Since dose may be varied by location within a same tumor to account of heterogeneity of the tumor, the probability of proper application may affect the success of treatment. In other embodiments, no additional probabilities are used. In another alternative, separate models are provided, such as separate probabilities. The outputs or probabilities may be combined.

In one embodiment, a normal tissue complication probability is modeled. The model may be different for different types of tissue. For example, a model is learned for the lung. A simple model may presume that all parts of normal tissues have the same functional capacity. Every voxel has the same function and contribution to the global organ function. This simplification may not be used in other embodiments. For example in lungs, gas diffusion only occurs in the alveoli, and there is a large heterogeneity in the functional areas of the lungs because of different ventilation and perfusion. This is true in healthy individuals, and increases in lung diseases such as COPD and lung emphysema.

Magnetic resonance imaging (MRI) may show local ventilation using the inhalation of hyperpolarized gases or gadolinium aerosol. Low-field MRI may be used for static imaging of the lung. Mathematical processing of data derived from serial MRI scans during the respiratory cycle may produce good quality images of local ventilation without any contrast agent. Pulmonary function tests may correlate well with MRI ventilation measurements. Small ventilation defects may be visualized. MRI techniques also allow to visualization of the heterogeneity of lung perfusion. This information is used to determine probabilities associated with different types of healthy tissue regions. The probabilities may indicate a relative importance, such as attempting to limit marginal dose in areas having a higher probability of relatively important function. The probabilities may indicate a susceptibility to particular doses, such as some regions of healthy tissue being more susceptible to marginal dose. The probabilities are learned from functional imaging data, such as the MRI discussed above.

In another embodiment, uncertainty in dose delivery probability is modeled. The dose a location will receive has some uncertainty even given a specific applied dose. The dose to a location depends on whether or not the location is properly aligned with the linear accelerator at the time the radiation is administered, the location's position in space, the location's position relative to the rest of the patient, and the radiation fluence entering the patient. These parameters are unknown at the start of treatment. Even assuming that, after treatment, all this information is available, the accuracy of the calculation and summation of the dose to that voxel over multiple fractions may not be correct. The probability distribution of voxel dose is thus wide at the start of treatment and may be narrowed during treatment, depending on the type and amount of information collected during treatment.

Using data from before, after, and/or during treatment, a model of the probability of dose uncertainty may be learned by the processor 12. The probability is determined for tumor locations and healthy tissue locations. The feature vector may include dose, the size and shape of the tumor, and specific information of the linear accelerator. The feature vector can be combined linearly or non-linearly, and a probability value can be obtained for each voxel using, e.g., a logistic transformation. In other embodiments, the probability is determined by measurements or other techniques without machine learning. For example, the probability may be determined from data associated with a specific linear accelerator.

Figure 4:
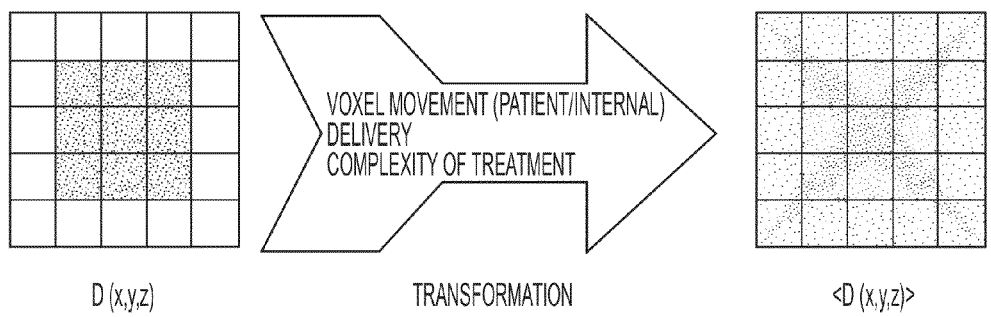
FIG. 4 is a graphic showing dose probability due to various factors in one embodiment.

FIG. 4 shows one example of dose probability. A 9×9 2D representation of dose to be applied is shown as dark boxes. The one-box margin of healthy tissue is shown. Due to displacement or other factors, the actual dose likely to be applied to any of the twenty-five regions may be different. These factors are accounted for by machine learning or other calculation represented as the transformation. The probability may account for all or any sub-set of factors. The right image shows the probability distribution. For a given box, probability is determined. The probability may be a function of the probabilities and/or intended dose levels for surrounding boxes.

Figure 5:
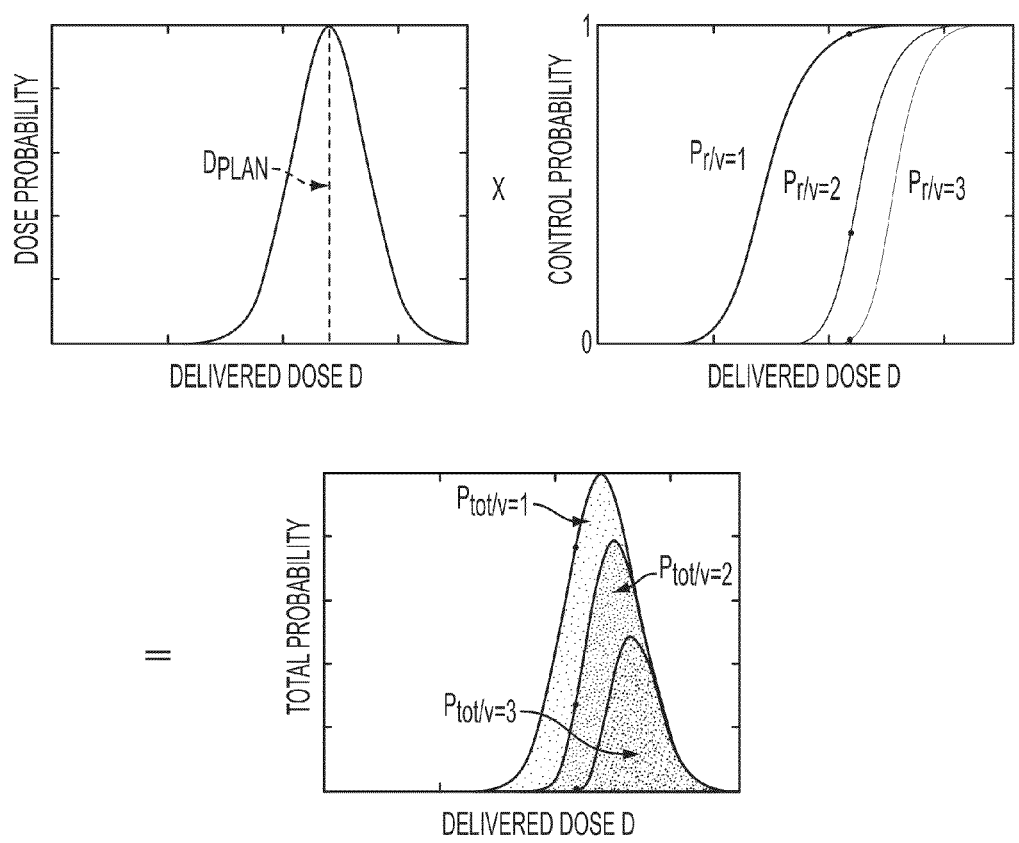
FIG. 5 shows one embodiment of combining dose and control probability.

The various models may be combined. For example, FIG. 5 shows the dose probability (i.e., probability of the desired dose being applied at a given location) and the control probability (i.e., the probability of residual disease given a dose) being combined into a total probability. Additional probabilities may be combined. A model may be trained to provide the total probability without a specific combination of other models or probabilities. In other embodiments, only one of the models or corresponding probabilities is created.

Dose painting may be based on a double or triple probabilistic approach per location. Uncertainty in dose is combined with uncertainty in response in the tumor locations and/or healthy tissue locations. In current radiotherapy practice, the uncertainties in tumor delineation, position, and shape as well as uncertainties in the delivery and planning phase of radiotherapy are taken into account by the safety margin applied to the delineated gross tumor volume. The uncertainty in both the content and dose to a region are considered. For example, the locations in the safety margin are assigned to contain clonogenic cells not because they might contain clonogenic cells, but to make certain that voxels within the gross tumor volume receive the correct radiation dose. On the other hand, the dose to a tumor location is incorrectly deemed a certainty in the current radiotherapy planning process. The margin approach has been very useful in daily radiotherapy practice and may be used with the probability of residual disease.

In the margin approach, in current radiotherapy, tumors are assumed homogeneous and that a uniform dose distribution is the best way to treat a tumor. As uncertainties in dose occur mostly around gradients in dose, the dose uncertainty in a uniform dose distribution is located at the edges of the tumor or uniform dose area. With the margin approach, this is exactly the area where the safety margin is applied. In the case of a heterogeneous tumor treated with multiple dose levels (e.g. dose painting) at the respective locations, gradients between dose levels and thus the dose uncertainties occur within the tumor. To account for these uncertainties with a margin, a margin is applied for each of the heterogeneous zones or even for each voxel location within the tumor. Conflicts may result between doses for different voxels. In addition, the size of the margin may depend on the dose gradient (i.e. a large dose gradient requires a large margin) between the regions, so may be a result of the planned dose rather than an input for the planning process.

As an alternative to the margins approach for heterogeneous dose distribution, the probability modeling is provided. For example, a model is built to predict, at each voxel level (e.g., SUV uptake range), the SUV value 90 days after the treatment. For each voxel, the information from nearby voxels (e.g. their SUV values, shape of the gross tumor volume (GTV) at the specific voxel) is considered in building the predictive model. The model is based on dose and control probabilities for both healthy tissue locations and different tumor locations. The probabilities determined for normal tissue are of complication. The model may consider other clinical factors, such as age and gender.

In the lung cancer database example discussed above, a model may be trained. Of the 95 patients, some patients, such as four patients, may be excluded from the training data because of large deformations of the tumor. The remaining patients have residual disease at some level or not. For example, twenty-four patients have a residual three months after therapy. Any variation in probability by level may exist, depending on the training dataset. For example, below an $SUV_0$ of 5, the probability of residual disease increases with increasing $SUV_0$ for each patient. The maximum probability may occur at an SUV of 8. For $SUV_0 > 10$, the probability may increase or decrease. For example, the probability decreases due to a limited sampling (e.g., only three patients having an FDG uptake values above 10).

The probability of residual disease in a tumor voxel depends on the corresponding SUV before therapy. Variation between different patients may be expected and may arise from differences in delivered dose, tumor volume, and integral SUV uptake (total SUV uptake for the whole tumor). The influence of these parameters on the probability of residual disease may be included in the model as part of the feature vector such that the probability accounts for these factors.

The processor 12 applies the model or models. The probabilities are used to determine the dose for each location. For example, the radiation level is determined to be different for different ones of the tumor regions. Given an overall dose, the dose is redistributed amongst the different regions as a function of the tumor response. Functional imaging information for a given patient indicates the tumor response. Using the probabilities, the dose to optimize the success or more likely avoid residual disease for each location is determined. The probability associated with the uptake of a given location is used. Using one or more models, with or without iteration, different doses for different regions are determined based on the probability of residual disease, the probability of normal tissue complication, and/or the probability of dose variation. Any optimization may be used. Other factors may be considered, such as applying probabilities determined for an appropriate age, gender, and/or other clinical information grouping.

In one embodiment, the functional imaging data, clinical information, dose, and/or other data of relevant feature vectors is input into the model or models. The probability of success is output. Different doses may be input until a desired probability of success is output for each location. The model may receive dose levels for each location so that the dose gradient may be used to determine the probability. Other limitations on the model, such as a probability of normal tissue complication, may be imposed on the model. In other embodiments, the dose is determined by using the probabilities without determining a specific probability for a given patient based on input to the model. The model instead is represented by or incorporates the probabilities. The dose for a location is selected based on the probability curve. Iterative or other approaches determine the localized doses that satisfy any criteria, such as minimization of normal tissue complication and maximization of probability of success given threshold limits on each.

The processor 12 assists the medical professional to create a treatment plan, which gives the best treatment (e.g., the highest chance of tumor control at acceptable complication probability). The question may be split into two sub-parts: the probability "$P_v(d)$" that a dose d is delivered to a voxel v given the treatment plan, and the expected probability "$P_{r/v}(d)$" of an effect (complication or tumor relapse) in each voxel given a delivered dose d to the voxel. The probability of response in a certain voxel "$P_{r/v}(d)$" may be modified by one or more factors, such as factors "c" and "s" taking into account, respectively, the effect of a clinical factor (e.g., tumor size) and a systemic treatment (e.g., concomitant chemotherapy and biological modifiers). Given the probability distribution of dose and the biological properties of the voxel, the expected tumor control and complications in that voxel, "$P_{tot/v}$," in the organ and for the patient as a whole may be determined.

The expected probability of tumor control and complications may be described by the integral of the product of the two probabilities over the dose d:

$$P_{tot/v} = \int_d P_v(d) \cdot P_{r/v}(d) \, dd. \quad (1)$$

The interaction between the various voxels may be included in the probability determinations. For an organ, the expected control probability is the product of "$P_v$" for all voxels in the organ:

$$P_{tot/Organ}^{Control} = \prod_{v \, in \, Organ} P_{tot/v}^{Control} \quad (2)$$

and the expected organ complication probability is $$P_{tot/Organ}^{Complication} = 1 - \prod_{v \, in \, Organ} \left(1 - P_{tot/v}^{Complication}\right). \quad (3)$$

Figure 6:
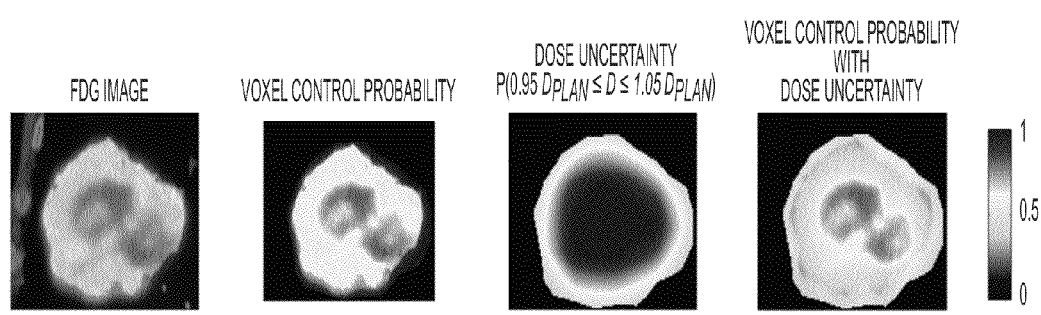
FIG. 6 shows a functional image, a corresponding control probability image, a corresponding dose uncertainty, and a combined probability for dose determination.

Similar equations hold for the final NTCP-TCP for a patient, although the product is taken over all relevant voxels in the patient. Combining both probabilities is illustrated schematically in FIGS. 5 and 6.

The NTCP-TCP may be a relative probability, such as the probability of relapse in high SUV areas compared to low SUV areas. The relative probability may be used for redistribution of dose in a particular patient. The NTCP-TCP may be an absolute probability, allowing comparison of various patients. For absolute or relative probability, additional factors, such as genetic factors, may be accounted for or included in the model calculation of the probabilities.

Therapeutic strategies may integrate systemic treatment, such as chemotherapy or targeted drugs. These treatments may modify the TCP-NTCP of radiation treatment. The probability may be modified:

$$P_{tot/v} = \int_d P_v(d) \cdot P_{r/vs}(d) \, dd \quad (4)$$

where the probability of response in a certain voxel "$P_{r/v}(d)$" is modified by a factor "s" taking into account the effect of a systemic treatment. Using machine learning, other factors may be input as features and the resulting probabilities or model learned.

A model, probability, or a model using a probability is provided for dose planning. The voxel control-complication probability may be a value, a set of values, a curve, a set of curves, or part of a classifier matrix. The probability and/or model are quantitative, linking biology to physics with the ability to adapt the radiation treatment with "dose painting" (determining dose differently for different regions of the tumor). Any imaging technique and/or functional hypothesis (e.g., hypoxic cells are more radio resistant) may be used. Clinical variables, such as tumor size or grade, may or may not be integrated. Systemic treatments may be integrated. Using machine learning is flexible enough for further improvement, such as improvement by modifying the probability of a certain effect based on genetic factors or integrating imaging during treatment.

To apply the model or probability, functional or fused images (e.g., CT-PET) are acquired before and/or during treatment. The functional imaging information is used with an "imaging based VCP" to show the effects of a planned or possible dose. The planned or possible dose may be heterogeneous or homogeneous. Dose probability is mapped on the tumor and the normal tissues, providing a "dose distribution based VCP." Both probabilities are integrated, providing an "imaging-dose based VCP." Further refinements are possible by taking into account the effect of systemic treatments and other biological or genetic factors.

Biological imaging, probability of dose distribution, and/or probability of resistance in relation to tumor and normal tissue heterogeneity allow probabilistic-based oncology. The combination of voxel control for the tumor, voxel complication for normal tissues, and voxel dose probability may allow treatment better modeled to the individual patient and increased optimization for better outcome.

Referring to FIG. 1, the processor 12 outputs the probabilities, dose, dose distribution, functional image, structural image, charts, values, plan, and/or other information for creating or using the models. The processor 12 outputs the data to the memory 14, over or to a network, to a printer, or in other media.

The output and/or inputs may be displayed to a user on the display 16. The display 16 is a CRT, LCD, plasma, projector, monitor, printer, or other output device for showing data. The display 16 is operable to display medical images, a user interface, charts, graphs, values, or other information, such as the probabilities and/or dose distribution. For example, the display 16 outputs an image generated as a function of the tumor response to a dose plan. The image shows the predicted residual disease and/or probabilities. The display is text, graphical, or other display. Supporting information, such as values, different model outputs, options, or other supporting information, may be displayed.

The processor 12 operates pursuant to instructions. The instructions, image data, clinical data, and/or patient record for distributing dose for tumor treatment are stored in a computer readable memory, such as external storage, memory 14 (e.g., cache, system memory, ROM and/or RAM). The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The same or different computer readable media may be used for the instructions, the individual patient data, the model, and the database of previously treated patients. The patient records are stored in the external storage, but may be in other memories. The external storage or the memory 14 may be implemented using a database management system (DBMS) managed by the processor 12 and residing on a memory, such as a hard disk, RAM, or removable media. The external storage may be implemented on one or more additional computer systems. For example, the external storage may include a data warehouse system residing on a separate computer system, a PACS system, or any other now known or later developed hospital, medical institution, medical office, testing facility, pharmacy or other medical patient record storage system. The external storage, an internal storage (memory 14), other computer readable media, or combinations thereof store data for at least one patient record for a patient. The patient record data may be distributed among multiple storage devices.

In other embodiments, the system 10 connects with a structural imaging system, a functional imaging system, and/or a therapy applicator (e.g., linear accelerator). For example, the system 10 connects with a CT-PET system and a linear accelerator for radiation therapy. The imaging system scans the patient and provides data representing the scanned region of the patient for transformation by analysis. The system assists the user in planning therapy given the functional imaging information, outputting images with values, charts, and/or images representing information about the patient. The system 10 is part of one of these components and/or communicates with the components to acquire image data and control treatment. For example, the processor 12 communicates a fraction of a treatment plan to the linear accelerator, controlling application of radiation to the patient.

Figure 7:
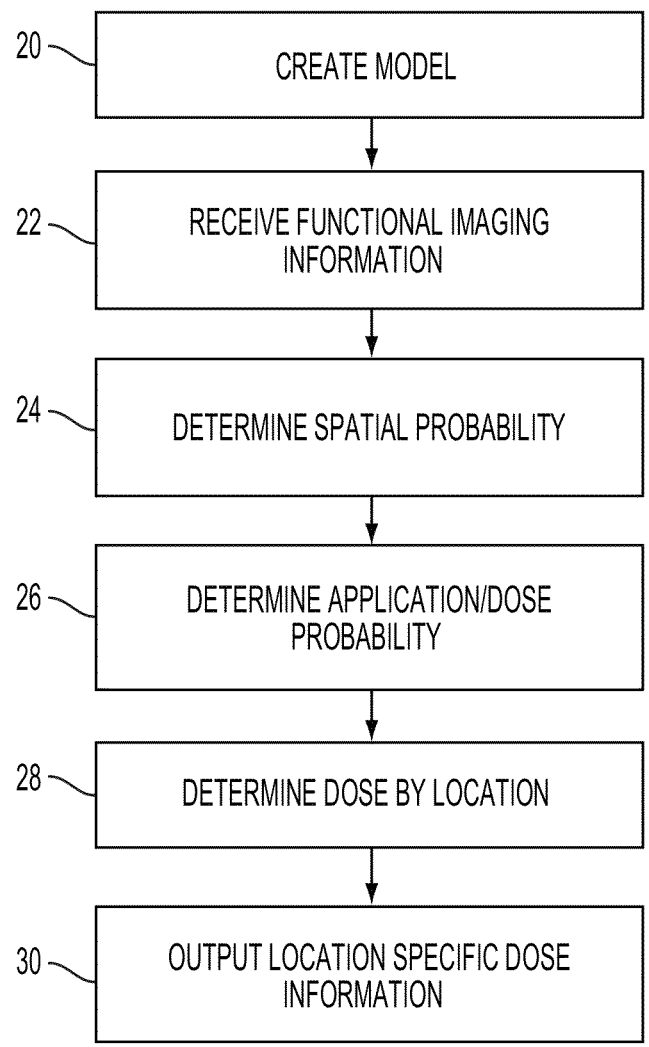
FIG. 7 is a flow chart diagram of one embodiment of a method for modeling dose distribution.

FIG. 7 shows a method for modeling dose distribution. The model is created and/or applied using patient information, including functional imaging information. Any other patient information may be used, such as characteristics, treatment, imaging, tumor and/or other information. Patient characteristics may include age, gender, co-morbidities, performance score (WHO, Karnofsky) or others. Tumor characteristics may include Staging (e.g., tumor-node-metastasis (TNM) staging, according to the American Joint Committee on Cancer, AJCC), size, shape, number, location, histology, or others. Treatment information may include regime, dose, time, type, medicine, or others. Imaging information may include gross tumor volume (GTV), standard uptake value (SUV), or others.

The method is implemented with the system of FIG. 1, or a different system. The same or different systems may perform the creating and applying stages. For example, one computer is used for development, and a different computer is used for applying the developed models. The models may be developed, and then sold or otherwise distributed for application by others. As another example, the use of the developed models is charged. Users request predictions from the developer, so the model is applied by the same computer used for development or by different computer controlled by the developer.

The acts are performed in the order shown or a different order. Additional, different, or fewer acts may be provided. For example, acts 20, and 26-30 are not provided. As another example, development act 20 is performed without the application acts (22-30) or vice versa. In another example for application, acts 22-26 are provided to assist in planning without determination of a dose in act 28.

In act 20, the model is created. The model is created as discussed above, such as machine learning using a training data set. The model may be created using any type of functional data indicating spatial variation. Any number of patients may be included in the training data. The data is labeled as appropriate for the desired outcome. The machine-learning algorithm or algorithms are selected. Any now known or later developed algorithm and process for training may be used.

The training information corresponds to the information used for application of the model. Functional image information is obtained with any desired additional information, such as dose, clinical information, application information, or other data. One or more models are trained, such as determining probabilities for residual disease and determining dose or application probabilities. The models may be combined or maintained separately.

The created model or models are validated. A five-fold or other cross validation is performed on patient-data. Any validation may be used.

Once created, the model or models are incorporated onto a computer, such as into hardware, software, or both. The incorporation allows operating, with a processor, combined models or a single model for an individual patient. Values for the predictors of the models are obtained. The medical record, functional imaging data, and/or other source provides values for a specific or individual patient. The model is applied to the individual patient information.

In act 22, functional imaging information is received. The information is obtained from a scanner. Alternatively, the information is obtained from memory, such as previously acquired data transferred from a PACS database.

The functional imaging information indicates spatial distribution of function of tissue. Any function may be identified, such as glucose uptake using FDG. Protein tags or other binding agents may be used to identify function. Contrast agents may be used. More than one type of function may be identified, such as using multi-spectrum approaches. In one embodiment, positron emission information showing variance of standardized uptake of different locations in a cancer region and/or a margin of normal tissue is obtained. The standardized uptake may be of fluorine-18 deoxyglucose or other agent. In other embodiments, image processing without agents or tags identifies function of the tissue.

The functional information shows different function at different portions of the tumor or other tissue. For example, a PET scan of FDG shows uptake by glucose in the lung tissue. Different locations within a tumor and/or a margin correspond to different levels of glucose. The locations may be of any size. In one embodiment, the functional imaging data includes voxels representing three-dimensions. Each voxel is treated as a different location. The scan settings determine the voxel size. In other embodiments, the region or location is larger than the voxel. Data from multiple voxels is combined to determine the functional information for that location of the tissue.

The functional information, such as the imaging data of the uptake of an agent, is acquired from a time before a current treatment of the patient. For example, the functional information is acquired hours, days, or weeks prior to therapy. Alternatively, the functional information is acquired during treatment, such as between fractions of a therapy plan or interleaved with the application of therapy.

The functional information is received in response to a request. For example, the processor 12 requests acquisition of the data by a scanner or from a database. In response, the requested information is transferred to and received by the processor 12. Alternatively, the functional information is pushed to the processor 12. The receipt may occur in response to user input or without direct user input.

Other feature vector information is received. The data input corresponds to the predictors or variables used by the models. For example, functional imaging data indicating importance or susceptibility of normal tissue is received.

The data is input manually. Alternatively, the data is mined from a database. A processor mines the values from a medical record of the individual patient. For example, the mining discussed in U.S. Published Application No. 2003/0120458, the disclosure of which is incorporated herein by reference, is used. Structured clinical data is mined from unstructured and structured information. If values are available from unstructured data, the values may be mined by searching or probabilistic inference. Other mining may be used, such as acquiring data from a structured computerized patient record (CPR). The mined and/or manually input values are applied to the combined models to obtain a probability, dose, or other information.

Where a value for an individual patient is not available, a value may be assumed, such as using an average. Alternatively, the field may be left blank. For example, one of the questions asked is whether the patient is a smoker or not. If there is no evidence provided in the patient record if the user is a smoker, then the system leaves this blank or records that the user is a smoker, since the prior probability (based on the percentage of smokers) suggests that the lung cancer patient is probably a smoker.

In act 24, the spatial probability is determined. The probability predicts therapy responses of the cancer and/or normal tissue region at the different locations. The spatial probability is predicted as a function of the standardized uptake for the respective different locations. The uptake or other functional information indicates therapy effectiveness or resistance. The model indicates the likelihood of residual disease a given time period after application of a given dose. Since different function levels are provided for different locations, the probability is determined for each of the locations.

The model may be for any type or combination of types of treatment. Treatment may be a lack of further action, chemotherapy, type of drug, amount of drug, radiation, type of radiation, radiation timing, or other treatment, or treatment combination.

The patient specific information is input to the model as values for variables of the feature vector. The probabilities for each of the different portions are classified with a feature vector. The feature vector for one portion may include the uptake for the portion, uptake for surrounding ones of the different portions, a size of the tumor, and/or at least one clinical factor. Clinical factors may include gender, overall stage, gross tumor volume (GTV), performance scale (WHO-ps), histology, age, nicotine use, chemotherapy, forced expiratory volume in 1 sec (in liter), T-stage, and/or other variables. The information from the surrounding portions, such as the uptake for surrounding portions and/or dose of the surrounding portions, may affect the probability. The tissue response is modeled as a function of the probability of residual disease given the standardized uptake at the region, the location specific radiation dose, the standardized uptake at neighboring ones of different locations, a patient age, a patient gender, and/or size of the cancer region. Standardized uptake is used to normalize, such that data from different patients may be used.

The application results in one or more probabilities. The determination of the probability classifies response of the different portions of the tumor and/or normal tissue as a function of the uptake for the different portions. Control probabilities of residual disease given a dose are included in the model to determine the probabilities for the patient. The control probabilities were machine-learned from a training dataset for other patients having uptake information before and after treatment by radiation.

The probabilities may be based on the uptake value with any resolution. For example, ranges of uptake values are modeled separately. Any step size or range grouping may be used. For a given range, the control probabilities indicate the likelihood of residual disease given a dose. Separate probabilities may be given for tumor tissue and normal tissue. In one embodiment, the tumor control probability is modeled as a function of dose and range of uptake, and a normal tissue control probability is modeled as a as a function of dose. The probability of normal tissue complication is determined.

In act 26, the application probability is determined. Due to various factors, the likelihood of the dose being applied to a given location is less than 100%. The probability of dose application may be calculated. The dose actually applied may vary, in part, due to the dose to be applied to adjacent locations. Using adjacent dose levels and other features, the probability of correct dosage is determined as a function of spatial location.

The probabilities may be combined. For example, the probabilities are determined separately. The probabilities for a given location may be combined to determine an overall probability given various features or variable values for a specific patient. Alternatively, the overall probability is determined, such as one model performing acts 24 and 26.

The probabilities are output to the user. A table, image, or other image may be used to communicate the likelihood of effect of the possible treatment selected by the user. The user may select different treatment plans, types of treatment, and/or alter treatment parameters based on the probabilities. The probabilities may alternatively be input to a dose calculation algorithm on the same or a different system using a same program or a separate program for dose determination.

In act 28, dose information is determined. In addition to or as an alternative of outputting probability information to the user, the probabilities are used to optimize the dose. The probabilities are used for dose planning. The dose to be applied to different locations in the tumor is determined as a function of the radiation response of the patients tissue based on the functional imaging information. Since the radiation response varies by region, the dose may likewise vary by region.

Any solution may be used. In one embodiment, different dose adjustments are made automatically. In response to each variation, the probabilities, based at least in part on the tissue response for the patient, are determined as a function of the proposed new dose or doses.

The process continues iteratively to identify the dose by region combination providing an optimal solution or treatment. Alternatively, the graphs of probability variation with dosage are analyzed to determine the desired dose.

The optimal solution may be defined by the user or predetermined. For example, the optimal solution is very low probability (e.g., less than 5% probability) of residual disease with very low normal tissue complication (e.g., less than 5% probability). The user may adjust the thresholds for acceptable residual disease probability and normal tissue complication probability. The solution providing the least number of locations with a threshold probability of residual disease or the least average probability of residual disease is determined. The probability of proper dose may be used to weight the determination of the optimal solution.

The dose levels as a function of location with sufficient probability of success and sufficient lack of probability of harm to normal tissue is determined. The determination is based on the uptake or functional information at the different portions of the tissue.

The dose is an absolute value, such as a specific total Gy value. Alternatively, the dose is shown as an increase or decrease. For example, the dose determination is a recommendation of locations to increase and decrease dose as a function of predicted therapy response. This information may be used to select the desired therapy or to allow user-based alteration of the plan.

The determined dose varies as a function of location. The same overall dose may be provided, but redirected to more likely treat the tumor. The overall dose may be decreased, reducing risk to normal tissue, with a same or better likelihood of treatment of the tumor. For any dose level, the risk to normal tissue may be decreased due to lower dose levels at the edge of the tumor where the edge is more susceptible to the therapy. The overall dose may be increased, but with less or the same risk to normal tissue.

In act 30, the location specific radiation dose is output for each of the different locations of the cancer region. Different location specific doses are output for the different locations.

The dose is output to a display. The display is an image representing tissue coded or modulated to indicate dose level. Alternatively or additionally, the output is an image of a report indicating the dose level by spatial location. A table, graph, or other output may be provided.

The output is to a display, such as an electronic display or a printer. The output may be stored in memory or transferred to another computer. In one embodiment, the dose information is output for use with a linear accelerator to treat the patient. The dose information is included in a treatment plan. The doses are fractionalized and provided to control the linear accelerator. In response, the linear accelerator applies radiation to the tumor regions.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for modeling dose distribution, the system comprising:
   an input operable to receive functional imaging information representing metabolic or biochemical activity of a tumor;
   a processor operable to apply a model of tumor response to a treatment dose, the tumor response being different for different regions of the tumor as a function of the functional imaging information, wherein the model represents a probability of residual disease after treatment in each of the different regions given the functional imaging information; and
   a display operable to output an image as a function of the tumor response.

2. The system of claim 1 wherein the input comprises a data interface operable to receive the functional imaging information.

3. The system of claim 1 wherein the functional imaging information comprises positron emission tomography imaging with fluorodeoxyglucose, the metabolic or biochemical activity comprising glucose metabolism, and the tumor being a tumor of a non-small cell lung cancer.

4. The system of claim 1 wherein the model is a machine-learned model.

5. The system of claim 1 wherein the model represents the probability of residual disease after treatment in each of the different regions given the functional imaging information and the treatment dose for the respective region.

6. The system of claim 5 wherein the probability is a function of data from other patients representing functional imaging information before and after radiation therapy at known dosages.

7. The system of claim 6 wherein residual disease after treatment corresponds to functional imaging information, from after radiation therapy, greater than a threshold standard uptake value for the respective patient, the threshold standard uptake value for each patient being a function of the functional imaging information for that patient.

8. The system of claim 1 wherein the model uses a feature vector comprising age, gender, performance score, and tumor size.

9. The system of claim 1 wherein the model uses a feature vector for each of the different regions, the feature vector comprising functional imaging information from neighboring ones of the different regions.

10. The system of claim 1 wherein the processor is operable to determine radiation level differently for different ones of the different regions.

11. The system of claim 1 wherein the processor is operable to redistribute the treatment dose amongst the different regions as a function of the tumor response.

12. In a non-transitory computer readable storage medium having stored therein data representing instructions executable by a programmed processor for distributing dose for tumor treatment, the instructions comprising:

receiving positron emission information showing variance of standardized uptake of agent at different locations in a cancer region;

predicting a probability for therapy responses of the cancer region at each of the different locations as a function of the standardized uptake for the respective different locations;

determining an increase or decrease in a location specific dose as a function of the predicted therapy response; and outputting the location specific dose for each of the different locations of the cancer region.

13. The non-transitory computer readable medium of claim 12 wherein receiving positron emission information comprises receiving positron emission information showing the variance of standardized uptake of fluorine-18 deoxyglucose.

14. The non-transitory computer readable medium of claim 12 wherein predicting comprises modeling as a function of a probability of residual disease given the standardized uptake and the location specific dose.

15. The non-transitory computer readable medium of claim 14 wherein modeling comprises modeling as a function of the standardized uptake at neighboring ones of different locations, a patient age, a patient gender, and size of the cancer region.

16. The non-transitory computer readable medium of claim 12 wherein outputting comprises outputting different location specific doses for the different locations.

17. A method for modeling dose distribution, the method comprising:

determining uptake of an agent at different portions of a tumor in a patient from emission tomography information;

classifying, with a processor, radiation response of the different portions of the tumor as a function of the uptake for the different portions and control probabilities of residual disease given a dose, the control probabilities of residual disease having been machine-learned from a dataset for other patients having uptake information before and after treatment by radiation;

determining dose information as a function of the radiation response, the dose information varying between the different portions of the tumor; and outputting the dose information for use with a linear accelerator to treat the patient.

18. The method of claim 17 wherein determining uptake comprises determining uptake of fluorodeoxyglucose from a positron emission tomography image of the patient's lung, wherein classifying comprises modeling a tumor control probability of residual disease as a function of dose and range of uptake, and a normal tissue control probability of residual disease as a function of dose, wherein determining dose information comprises determining dose levels with sufficient probability of success and probability of harm to normal tissue as a function of the uptake at the different portions.

19. The method of claim 17 wherein the uptake is from a time before treatment of the patient.

20. The method of claim 17 wherein classifying comprises classifying for each of the different portions with a feature vector comprising the uptake for the portion, uptake for surrounding ones of the different portions, a size of the tumor, and at least one clinical factor.

21. The method of claim 17 wherein classifying comprises classifying as a function of probabilities of proper application of dose.

22. The system of claim 1 wherein the model comprises dose probabilities.

23. The non-transitory computer readable medium of claim 12 wherein predicting comprises predicting as a function of a dose uncertainty.

* * * * *